United States Patent
Sengelaub et al.

(10) Patent No.: US 10,437,327 B2
(45) Date of Patent: Oct. 8, 2019

(54) EYE TRACKING DEVICE AND METHOD FOR OPERATING AN EYE TRACKING DEVICE

(71) Applicant: APPLE INC., Cupertino, CA (US)

(72) Inventors: Tom Sengelaub, Berlin (DE); Martin Haller, Berlin (DE); Jan Hoffmann, Kleinmachnow (DE)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 15/571,966

(22) PCT Filed: May 4, 2016

(86) PCT No.: PCT/EP2016/059996
§ 371 (c)(1),
(2) Date: Nov. 6, 2017

(87) PCT Pub. No.: WO2016/180702
PCT Pub. Date: Nov. 17, 2016

(65) Prior Publication Data
US 2018/0120932 A1    May 3, 2018

(30) Foreign Application Priority Data
May 8, 2015   (EP) .................................. 15167021

(51) Int. Cl.
*G06K 9/00*   (2006.01)
*G06F 3/01*   (2006.01)
*A61B 3/113*   (2006.01)
(52) U.S. Cl.
CPC .............. *G06F 3/013* (2013.01); *A61B 3/113* (2013.01); *G06K 9/0061* (2013.01); *G06K 9/00604* (2013.01)

(58) Field of Classification Search
CPC .. G06K 9/00604; G06K 9/0061; G06F 3/013; A61B 3/113
See application file for complete search history.

(56) References Cited

U.S. PATENT DOCUMENTS 6,634,749 B1   10/2003   Morrison et al.
2007/0216787 A1*   9/2007   Lin .................... H04N 5/23212
                                                    348/252

(Continued)

FOREIGN PATENT DOCUMENTS

WO   9955220 A1   11/1999
WO   2015066475 A1   5/2015

OTHER PUBLICATIONS

International Search Report and Written Opinion for PCT/EP2016/059996 dated Jul. 13, 2016.

(Continued)

*Primary Examiner* — Amara Abdi
(74) *Attorney, Agent, or Firm* — Fernando & Partners, LLP; William J. Higley (57) ABSTRACT

The invention relates to an eye tracking device (10*a*; 10*b*; 10*c*) comprising a processing unit (18) and an optical system (14), which comprises a capturing unit. The optical system (14) provides a first optical path (P; P1) with a first imaging property and a second optical path (P; P2) with a second imaging property and the capturing unit (C; C1, C2) captures a first image (24*a*) by capturing light that has passed along the first optical path (P; P1) and a second image (24*b*) by capturing light that has passed along the second optical path (P; P2), so that due to the difference of the first and second imaging property the first (24*a*) and the second image (24*b*) comprise a difference related to a characteristic of at least part of the first and the second image (24*b*), wherein the eye tracking device (10*a*; 10*b*; 10*c*) is configured to determine (Continued)

a property of the eye (12) on the basis of at least one of the first image (24*a*) and the second image (24*b*).

19 Claims, 4 Drawing Sheets

(56) References Cited

U.S. PATENT DOCUMENTS

| | | | | |
|---|---|---|---|---|
| 2011/0279666 A1* | 11/2011 | Strombom | ............. | A61B 3/113 |
| | | | | 348/78 |
| 2014/0049656 A1* | 2/2014 | Kimoto | ............. | H04N 5/23212 |
| | | | | 348/208.1 |
| 2014/0104490 A1* | 4/2014 | Hsieh | ................... | H04N 5/2252 |
| | | | | 348/375 |
| 2014/0139667 A1* | 5/2014 | Kang | ................ | H04N 5/23219 |
| | | | | 348/143 |
| 2014/0333521 A1* | 11/2014 | Hwang | ................... | G06F 3/013 |
| | | | | 345/156 |
| 2014/0375541 A1* | 12/2014 | Nister | ..................... | G06F 3/013 |
| | | | | 345/156 |
| 2016/0309081 A1* | 10/2016 | Frahm | .................... | G06F 3/013 |

OTHER PUBLICATIONS

International Preliminary Report on Patentability for PCT/EP2016/059996 dated Oct. 19, 2017.

\* cited by examiner

EYE TRACKING DEVICE AND METHOD FOR OPERATING AN EYE TRACKING DEVICE

The invention relates to an eye tracking device comprising an optical system, which comprises a capturing unit for capturing images of at least one part of at least one eye of a user. The eye tracking device further comprises a processing unit for determining at least one property of the at least one eye, e.g. the gaze direction, based on the captured images. Moreover, the capturing unit is configured to capture a first image and a second image of the at least one part of the at least one eye of the user. The invention also relates to a corresponding method for operating an eye tracking device.

There are different eye tracking devices known from the prior art, like remote eye trackers or head-mounted eye trackers, as well as different eye tracking methods, like appearance-based eye tracking or model-based eye tracking. Such eye tracking devices usually capture images of an eye of a user and determine certain features of the eye on the basis of the captured images. Usually, from these images a pupil position or iris position is determined. For example, the pupil position can be found by first searching for the pupil in the image and then calculating the pupil center, for example, by finding the center of the pupil contour points. Some eye trackers also use active illumination for producing cornea reflections on the eye. By assuming that the cornea surface is a sphere and by determining the position of two or more such cornea reflections the cornea center can be determined. Also, the gaze direction can be determined, for example, as a straight line through the cornea center and the pupil center. This straight line defines the optical axis of the eye and can be calibrated in a calibration procedure to take into account individual deviations of the line of sight from the optical axis of each individual user.

With regard to eye trackers and eye tracking methods in general there will always persist the need for enhancing accuracy and precision. The precision and accuracy of the gaze direction or other determined eye features mainly depends on how accurately eye features like the pupil or cornea reflections and their positions can be determined in the captured images. Moreover, as eye trackers get integrated in more and more devices, like computers, cars, virtual-reality-glasses, and so on, it's also a need to provide very compact eye tracking devices and offering much flexibility.

Therefore, it is an object of the present invention to provide an eye tracking device and a method for operating an eye tracking device by means of which high precision and accuracy can be achieved and by means of which the eye tracking capabilities can be enhanced.

This object is solved by an eye tracking device and a method for operating an eye tracking device with the features of the respective independent claims. Advantages embodiments of the invention are presented in the dependent claims.

The eye tracking device according to the invention comprises an optical system, which comprises a capturing unit for capturing images of at least one part of the at least one eye of a user, and the eye tracking device further comprises a processing unit for determining at least one property of the at least one eye based on the captured images, wherein the capturing unit is configured to capture a first image and a second image of the at least one part of the at least one eye of the user. Furthermore, the optical system comprises an imaging property, comprising at least one first imaging property and a second imaging property different from the first imaging property. Moreover, the optical system provides a first optical path with a first imaging property and a second optical path with a second imaging property. Furthermore, the eye tracking device is configured such that the capturing unit captures the first image by capturing light that has passed along the first optical path and the second image by capturing light that has passed along the second optical path, so that due to the difference of the first and second imaging properties the first image and the second image comprise a difference related to a characteristic of at least part of the first and the second image, wherein the eye tracking device is configured to determine the at least one property of the eye on the basis of at least one of the first image and the second image.

By providing different imaging properties, e.g. by different focal lengths, by one and the same eye tracking device, much more flexibility is provided for adapting to different situations. Moreover, thereby great advantages, especially with regard to accuracy and precision, can be provided. Especially, the invention is based on several findings: For example, different imaging properties can be provided by different focal lengths or different image planes. Usual eye trackers use fixed focus lenses with a fixed depth of field. A fixed depth of field is disadvantageous especially with regard to remote eye trackers, where the position of the user with regard to the camera may vary a lot. Therefore, the depth of field has to be large to be able to capture sharp images of the eye, even if the position of the eye with regard to the camera varies. For providing a large depth of field, the aperture of the camera has to be very small, which again leads to great losses of light and low light intensity for image capturing, which results in bad image quality and makes it difficult to determine eye features like the pupil in the image precisely. However, according to the invention, it is possible to have different imaging properties, which allows for example to focus on the eyes of a user without the need for a large depth of field. This again allows for larger apertures, a higher light intensity for image capturing, a higher image quality and therefore enhances precision and accuracy when determining the at least one property of the eye. Furthermore, it is another important finding of the invention that the position of a cornea reflection can be determined more accurately if unsharp or blurry images are used. If, for example, an in-focus image of the eye is captured, a cornea reflection appears in the image as a very small and bright point. However, depending on the situation or also on the resolution of the image sensor, a precise determination of the position of such a small point is difficult. Only small deviations of the determined point position from the actual position of the cornea reflection will lead to large errors in the finally determined gaze direction. If instead an out-of-focus image of the eye is captured, such a cornea reflection appears not as a point but as an extended circle, and it has been found that the determination of this circle center on the basis of the circle contour points leads to much better results with regard to accuracy and precision, especially as errors in determination of position of the contour points can be compensated much better when averaging these points, e.g. by fitting an ellipse to the found contour points, for determining the center of this contour. However, the situation is different when it comes to the determination of the pupil position. The pupil position instead can be determined the more accurately the sharper the image. Therefore, the invention also allows advantageously for using different imaging properties depending on the features to be determined. For example, sharp and unsharp images can be captured at the same time or successively and then the sharp images can be used for determining the pupil position and the unsharp images can be used for determining the position of the cornea reflection. The invention also has grate advantages with regard to an integration of the eye tracking device into other devices, especially a head mounted display, as in such a setup the different imaging properties provided by the optical system cannot only be used for enhancing eye tracking but also for projecting images of the display in a very advantages way, which is explained later in more detail. Therefore, optics of the eye tracking device can be shared with other devices, like a display device, which facilitates a compact integration of the eye tracking device in other devices.

Further great advantages of the invention are, for example, that one could use a focus sweep to estimate the depth of eye features, use intentionally unsharp images to blur out unwanted features, like undesired reflections on eye glasses of the user, or use actively the difference in the characteristic in the images to more easily identify certain features like cornea reflections. If, for example, light sources are provided for producing the cornea reflections on the eye of the user and the light sources illuminate the eye through the optical system with different imaging properties, the appearance of the cornea reflections in the captured images will vary accordingly and therefore can be more easily discriminated from environmental light.

So, by providing different imaging properties, many advantages can be achieved with regard to accuracy and precision, reducing losses of light and adaption to many different eye tracking situations.

The eye tracking device may be a head-mounted eye tracking device, like an eye tracking spectacle device, or an eye tracker integrated in a helmet or also integrated in a head-mounted display device, in virtual reality glasses, in augmented reality glasses or other head worn devices. The eye tracking device may also be a remote eye tracker, optionally integrated or coupled with other devices like a computer, displays, monitors, and so on. The capturing unit may comprise one or more cameras, light sensors, like image sensors, for example a CCD sensor or a CMOS sensor. In general, the processing unit may be a processor, a controller, a microcontroller or any kind of integrated circuit. The optical system can comprise any optical elements like one or more lenses, prisms, beam splitters, mirrors, reflectors, light guides, collimators, and so on.

According to a preferred embodiment of the invention, the first and second imaging property each relate to at least one of a focal length, a position of at least one element of the eye tracking device, in particular of the optical system, with respect to a reference position, especially an image distance, in particular a distance between at least part of the capturing unit, like an image sensor, and at least one optical element of the optical system, a distance between at least one light source of the eye tracking device and at least one optical element of the optical system, a degree of incline and/or rotation of at least one element of the optical system, especially of an optical element of the optical system and/or of an image sensor plane of the capturing unit, with respect to a reference position, and an aperture value.

The imaging properties of the eye tracking device may furthermore vary spatially or temporally. For example, the first and second optical path can be spatially separated, each path comprising a certain imaging property, for example by using lenses with different focal length in each of these paths. These optical paths of the eye tracking device also can be spatially identical and only vary with regard to their imaging properties in time, for example by using a lens, like a liquid lens, with a controllable and variable focus length or by moving the image sensor plane relative to a lens, e.g. parallel to a lens plane or by inclining the image sensor plane by an angle. For this purpose the capturing unit can comprise a normal camera or also a Scheimpflug-camera. By moving at least part of the capturing unit, the sharpness of the captured image can be influenced, as the sensor plan can be moved with respect to the focus plane, and also the view point or perspective can be changed. Also in case the imaging property varies temporally, the processing unit is preferably configured to control the imaging property, for example by controlling the focal length of a varifocal lens, by controlling the relative position of elements of the optical system, by controlling the opening or closing of an aperture diaphragm of the optical system, and so on. Also if light sources of the eye tracking device illuminate the eye through the optical system for producing cornea reflections on the eye, the light sources may be movable relative to the optical system and be controlled in their position by the processing unit, which influences the appearance, like size and shape, of the produced cornea reflections on the eye. Additionally or alternatively, the light sources, especially the emission characteristic and/or illuminance distribution provided by the light sources, can be influenced by at least one liquid lense, e.g. the more the liquid lens is focused the brighter the light sources shine, in particular the brighter are the cornea reflections produced by the light sources. In further embodiments the light sources, especially the emission characteristic and/or illuminance distribution provided by the light sources, are controlled via the processing unit by at least one parameter or a majority of parameters. Examples for the parameter and combinations of the parameter are the focal length of one or more liquid lenses and/or the voltage used to control the one or more liquid lenses. Finally, reciprocal the liquid lenses can be controlled by the processing unit by a parameter of the light source, i.e. voltage or brightness.

By providing such different settings with regard to the imaging property, this results in different image characteristics of the respectively captured images. These image characteristics preferably relate to a sharpness and/or range of sharpness and/or zoom factor and/or contrast and/or brightness and/or spectrum and/or saturation and/or size and/or shape of image features, which are the images of eye features in the captured image, and/or perspective and/or viewpoint of at least one part of the first and second image each. Differences in the images with regard to these characteristics can on the one hand be produced on purpose, for example to achieve a certain sharpness in the image or to optimize the contrast of image features, and on the other hand differences between the images relating to these characteristics can also be used to derive further information about the eye and eye features, e.g. using the difference in size of image features in different images, which results from different focal lengths, to calculate the distance of these eye features or the eye itself, the position of the eye or the size of the eye, i.g. the diameter from the capturing unit on the basis of this difference in size. The settings of the optical system and the change of the settings can also be controlled or triggered externally, e.g. by means of a control unit separate from the processing unit of the eye tracking device, e.g. by means of a control unit of a head mounted display, in which the eye tracking device is integrated. The processing unit then not necessarily has to be informed about the current setting or change in setting by the separate control unit for controlling the settings of the optical system, but also can derive information about the current setting or change in setting from image characteristics and/or difference in image characteristics of the captured images. Examples for systems and applications that can externally trigger the setting are commands, information or data sended or forwarded by medical devices, web interfaces, human interfaces or others.

Moreover, it is preferred that the at least one property of the eye is a position of the eye and/or an orientation of the eye and/or a gaze direction of the eye and/or other eye characteristics, like a characteristic of a pupil, limbus, iris or cornea reflections or any of dimension, size, shape, position, structure and/or orientation of such features.

According to another advantageous embodiment of the invention, the optical system is configured such that the direction of propagation of light propagating along the first path is altered in a first predefined manner, especially by refracting the light by a first predefined extent, and the direction of propagation of light propagating along the second path is altered in a second predefined manner, especially by refracting the light by a second predefined extent, wherein the first and second extent are different. Thus, different refractions of light can be achieved for example by a variable focus lens or by providing different paths each with lenses having a different focal length. These setups are very advantageous as there is no need for position variable elements. Thereby, mechanical exposure of the system can be reduced.

According to another advantageous embodiment of the invention, the processing unit is configured:

to derive the difference related to the characteristic, especially a sharpness and/or range of sharpness and/or zoom factor and/or contrast and/or brightness and/or spectrum and/or size of image features and/or shape of image features and/or perspective, of at least part of the first and the second image, and to derive first information about the at least one part of the at least one eye on the basis of the difference and to determine the property of the at least one eye on the basis of the derived first information about the at least one part of the at least one eye; and/or to analyse the first image and based on this analysis of the first image to predetermine a setting of the eye tracking device, so that the second image is captured comprising the difference with respect to the first image.

If, for example, the difference related to the characteristic is derived with regard to the sharpness, the zoom factor or the size of image features, which are features like the pupil or the iris in the captured image, wherein the difference with regard to these characteristics has been produced by different focal lengths, e.g. the size of these features in real life as well as their distance from the optical system can be calculated. Therefore, by analyzing the difference or change in the characteristics of captured images, depth information of eye features or the eye itself can be derived. It is also very advantageous to derive the difference related to the characteristic by subtracting the first and second image from each other. This way, especially contours of eye features can be determined very accurately, as small changes in sharpness, magnification or contrast especially have influence on the contours of features in the image. So, even if two unsharp images are used for determining the pupil position, if these two images are captured with slightly different focal lengths a subtraction of these unsharp images will show the resulting pupil contour very accurately. Also, the first image can be analyzed, for example with regard to a specific condition, like with regard to a sharpness condition, contrast condition, brightness condition, and so on, and if these image characteristics do not fulfil said conditions a new setting with regard to the imaging property of the optical system can be chosen such that said conditions are fulfilled. This way, images can be optimized, for example with regard to sharpness, contrast, and the other image characteristics, especially also with regard to the features to be determined from these images. As already mentioned, it might be advantageous to use unsharp images for the determination of the position of cornea reflections, whereas for determining the pupil position sharpness should be as good as possible.

According to another advantageous embodiment of the invention, the processing unit is configured to control and/or notify the optical system such that the first imaging property changes to the second imaging property, and the processing unit is further configured to take into account this change of the imaging property when determining the at least one property of the eye. This way, advantageously a compensation for the change in imaging properties can be provided and considered during eye tracking. If, for example, the capturing unit captures images of the eye through the optical system of the eye tracking device, which comprises a lens with variable focus length, a change in this focus length will also have an effect on the appearance of the image features in the respective images. So, e.g. the size of the eye or of the pupil changes in the image although the position of the eye with respect to the optical system does not change. A change of the imaging properties of the optical system therefore influences the size of image features, and moreover also their geometrical form, their sharpness, their contrast, brightness, and so on. So, knowledge of the imaging properties or at least of the change in imaging properties can be used for example to rescale detected image features in size or even in their form. Also, constraints for detecting certain image features can be modified in dependency on the imaging properties of the optical system. If, for example, images are analyzed to detect a pupil in the image, the processing unit searched for elliptical dark regions in the image, which have a certain minimum and/or maximum size. But as the colour, form and size properties of such image features can change due to a change in imaging properties of the optical system, it is advantageous to consider this by adapting the detection criteria correspondingly. So, with knowledge of the imaging properties or the change in imaging properties of the optical system, the impact of such change on the captured images can be compensated. Consequently, it can be avoided advantageously that a change in size of detected images features is misinterpreted as a change in position of the eye or eye features with respect to the optical system, or that images features are mistakenly not recognized as such in the image due to their changes in form, size or color spectrum.

Therefore, it is also a very advantageous embodiment of the invention when the processing unit is configured to determine the first information about the at least one part of the at least one eye in dependency on a known value of the imaging property. The first information again may be, for example, a size or position of an eye feature or cornea reflection, on the basis of which finally the gaze direction may be calculated. So, when determining the position, shape, size, distance of such eye features, it is advantageous to take into account the current setting of the optical system, in particular which constitutes the known value of the imaging property, of the optical system. However, this is also possible if the current value of the imaging property, like the current focal length is not known as such, as this value can be derived and calculated from the difference in characteristics of captured images, if the change of the imaging property is known only. If e.g. only the change in focal length is known and not the focal lengths as such, the corresponding values of the focal lengths can be calculated from the difference in in size of image features caused by the change of the focal length.

According to another advantageous embodiment of the invention, the processing unit is configured to control the optical system such that the imaging property changes in a predefined, especially alternating or varying, fashion, according to a preset variation pattern, especially to use one or more first images to determine a first eye feature and to use one or more second images to determine a second eye feature, e.g. to use images with a first sharpness value for determining a position of the pupil of the at least one eye and to use images with a second sharpness value, especially providing a lower sharpness than the first sharpness value, for determining a position of a cornea reflection on the cornea of the at least one eye, preferably wherein the at least one property of the eye is determined on the basis of the first and second eye feature. This way it can be achieved that for determining the position of cornea reflections, unsharp eye images can be used, whereas for determining the position of the pupil sharp eye images can be used. Finally, on the basis of the determined position of the cornea reflections, the cornea center can be calculated and in combination with the position of the pupil the optical axis can be determined. By using unsharp images for determining the cornea reflection position, a higher accuracy with regard to this position can be achieved and overall enhancement of precision and accuracy of the gaze direction can be provided. These advantages cannot only be achieved in a timely variation of the imaging properties of the optical system but also by locally or spatially varying imaging properties of the optical system.

So, in general it is a very advantageous embodiment of the invention when the processing unit is configured such that a first eye feature, e.g. a position of a cornea reflection on the at least one eye, is determined on the basis of the first image and a second eye feature, e.g. a position of the pupil of the at least one eye, is determined on the basis of the second image, especially wherein the at least one property of the eye is determined in dependency on the first and second eye feature. So, advantageously different images comprising different image characteristics, no matter whether they were captured at the same time or successively, can be used for precisely determining the position or shape of different eye features.

According to another advantageous embodiment of the invention, the eye tracking device is configured to determine on the basis of the difference whether the first image and/or second image is used for determining the at least one property of the at least one eye, preferably also to determine which part of the first image and/or which part of the second image is used. So, by capturing the first and second image with different imaging properties, the control unit may choose the better one, for example the sharper one, for determining the at least one property of the eye. Which of these images is used may also depend on the feature to be determined on the basis of this image, as already explained, for example, taking one of these images for determining the cornea position and the other one for determining the pupil position. Therefore, whether the first image and/or second image is used may depend on the different image characteristics themselves, like sharpness, intensity, contrast, and so on, or on the feature to be determined. Therefore, accuracy and position can be enhanced by always choosing the best image, and especially also by being able to actively produce images with different and more suitable characteristics by changing the imaging properties.

According to another advantageous embodiment of the invention, the processing unit is configured to provide a signal in dependency on the characteristic of at least part of the first and/or of the second image and in dependency on the signal to:
  set a parameter defining a value of the imaging property of the optical system, preferably to set the focal length and/or image distance and/or aperture value; and/or
  set a parameter in defining whether the first image or the second image is used for determining the at least one property of the eye; and/or
  determine the at least one property of the eye, preferably wherein the signal comprises information about at least one of a depth value or distance of the eye, for example a z-coordinate of the 3D position of the eye, and/or of the feature of the eye, especially a distance between at least part of the optical system and the eye and/or the feature of the eye, a 3D position of the eye and/or of the feature of the eye, an orientation of the eye and/or of the feature of the eye, the first and/or second imaging property, and a certainty value for the detection of the feature of the eye.

Therefore, on the basis of the characteristic of respective images or parts thereof, and especially also in dependency on changes of these characteristics from image to image or among different images, lots of information can be provided, especially with regard to the eye and eye feature itself, but also about current settings or states of the optical system itself. The above named certainty value here defines for a detected feature in the image, for example for a detected pupil, a probability that this detected image feature actually corresponds to the real eye feature, namely the real pupil to be detected. The difference in the image characteristics can also be used to enhance the certainty of feature detection. If, for example, light sources are used to illuminate the eye through the optical system, then a modification of the imaging property would also modify the appearance of the cornea reflections on the eye. This modification in appearance of the cornea reflections can finally be detected also in the captured images, so that cornea reflections can be more easily distinguished from environmental light. In other words, if reflections are detected in the captured images and the appearance of these reflections changes in accordance with changes of the imaging property of the optical system, it is very certain that these reflections are produced by the light sources of the eye tracking device and do not result from environmental light, which does not pass through the optical system with the modifying imaging property.

According to an advantageous embodiment of the invention, the optical system comprises at least one optical element, which is configured as or comprises a multifocal and/or varifocal element, like one or more lenses or prisms, and/or an position variable optical element configured to be variable in its positioning, especially wherein the eye tracking device, especially the processing unit, is configured to vary the position of the position variable optical element. For example, the position variable optical element can be a lens which is movable in its position with respect to the image sensor or the position variable optical element can be the image sensor which is movable in its position with regard to a lens. So, advantageously, by means of multifocal, varifocal or position variable optical elements different imaging properties can be provided.

According to another advantageous embodiment of the invention, the optical element comprises at least one first and/or second optical element comprising a first optical property, especially a first focal length or first surface structure, to refract light by the extent, thereby providing the first imaging property and/or a second optical property, especially a second focal length or a second surface structure, to refract light by the second extent, thereby providing the second imaging property. The first and second optical element may be, for example, a first and a second lens having different refractive powers, thereby providing the different imaging properties.

According to another example, the at least one first and second optical element can be positioned in the first and second optical path each. In this case, the first and second optical path are spatially separated, for example by means of a beam splitter, and each path provides different imaging properties due to the different focal lengths of the used lenses. Therefore, there are many possibilities of providing different imaging properties to be able to capture images of the eye having different image characteristics.

However, the most advantageous embodiment of this invention is to have an optical element, preferably a lens, which has a variable optical property, especially a variable focal length, and preferably is configured to provide the first imaging property when the variable focal length of the optical element is set to a first focal length and to provide the second imaging property when the variable focal length of the optical element is set to a second focal length. The use of such a varifocal lens, like a liquid lens, is very advantageous as different imaging properties can be provided in a very compact way, e.g. without the necessity of splitting up optical paths. Therefore, the number of necessary optical elements for providing different imaging properties can be reduced to a minimum. Such a varifocal lens also provides much more flexibility with regard to adjusting the imaging properties, as for example the focal length of such a varifocal lens can be adjusted continuously or at least in very small steps with high resolution.

According to another advantageous embodiment of the invention, the optical system is configured to provide the first and second imaging property temporarily successively, e.g. by above-named varifocal lens, preferably wherein the first and second optical path coincide spatially, or the optical system is configured to provide the first and second imaging property at the same time, wherein the first and second optical path are at least partially spatially separated, especially by means of at least one beam splitter. In this latter case, each path can be provided with different imaging properties, for example by using different lenses. Also, these spatial and temporal variations can be combined, for example by splitting up the optical path into two separate optical paths, one of which comprises again a varifocal lens, so that the imaging properties of the first path can be fixed and the other may be variable.

According to another advantageous embodiment of the invention, the eye tracking device is configured such that a capturing path extends from the at least one eye of the user to the capturing unit, wherein the capturing path comprises the first and/or second optical path, especially wherein the at least one optical element is positioned in the capturing path. This way, images of the eye can be captured by means of the capturing unit with different imaging properties. A change in the imaging properties automatically results in a change of all eye features captured in the image.

According to another advantageous embodiment of the invention, the eye tracking device comprises an illumination unit, comprising for example one or more light sources, and which is configured to illuminate the at least one eye to reduce a reflection on the at least one eye, especially a cornea reflection on the cornea of the eye, wherein the eye tracking device is configured such that an illumination path extends from the illumination unit to the eye, wherein the illumination path comprises the first and/or second optical path, especially wherein the at least one optical element is positioned in the illumination path. This way, the illumination of the eye can be varied according to the first and second imaging property provided by the first and second optical path. If, for example, the capturing unit captures images of the eye directly, namely without having optical elements providing different imaging properties in between, a variation of the imaging properties of the optical system will result in a change in appearance of only the cornea reflection in the image, leaving other eye features in the image unchanged. This setup can be used for more easily identifying cornea reflections or modifying the appearance of cornea reflections to enhance the accuracy of the determination of their positions.

These embodiments also can be combined, for example, if the one or more optical elements for providing different imaging properties are positioned in the illumination path as well as in the capturing path.

In general, the illumination unit may comprise one or more light sources, like LEDs or other light sources, for emitting light, preferably in the visible or infrared spectral range.

According to another advantageous embodiment of the invention, the eye tracking device comprises a display configured to display a display image. Furthermore, the eye tracking device is configured such that a display image can be seen by the at least one eye of the user through at least part of the optical system as a virtual image of the display image, so that the display image is imaged according to the first and/or second imaging property, thereby constituting the virtual image. Preferably, the eye tracking device is further configured to set a parameter such that the virtual image is displayed in a virtual display area, which corresponds to a determined depth of interest, preferably a vergence depth and/or accommodation cue, of the at least one eye, which can be e.g. determined by the eye tracking device. In particular, the display may be configured as a 3D display device, configured to display 3D images. For example the display can be configured as a pair of stereo displays, one of the stereo displays providing an image for the left eye and one of the stereo displays providing a display image for the right eye. However, also many other different techniques known from the prior art can be used for providing 3D display images, light using shutters or filters, etc. According to this advantageous embodiment, for example a varifocal lens can be used to display images of a head-mounted display as virtual images at different depths. At the same time, this varifocal lens can be used to enhance the eye tracking capabilities as well as accuracy and precision as described above. Especially, the varifocal lens and/or its different settings is used by the processing unit for a 3D reconstruction of the eye and/or eye features, e.g. for determining the 3D position of the cornea reflections, the 3D positon of the cornea center, the 3D position of the center of the pupil, the 3D gaze direction, and so on.

In this scenario, the focal length of the variable focus lens can be controlled to adapt the virtual display area corresponding to the vergence or accommodation of the user's eye. For a specific setting of the focal length, there exists a tolerance area, in which changes of the focal length would not be noticed by a user, for example within 0.2 dpt. This tolerance area can then be used to optimize the settings of the lens, especially the focal length within this tolerance area, with respect to eye features to be detected by the eye tracking device. Also the difference in focus, e.g. due to changes of the focal length within above named tolerance area, can be used for detecting and/or determining eye features, like the pupil contour or cornea reflection contour by subtracting images, which comprise a difference in focus, or by using sharper images for determining the pupil position and using less sharp images for determining the position of the cornea reflections, or using the difference in focus for deriving a depth information about the eye or eye features, like the distances of the eye from the eye tracking device or components thereof.

According to further advantageous embodiments of the invention, the settings of the eye tracking device for adjusting the imaging properties can also be chosen in dependence on the eye tracking algorithm currently used. For example, some eye tracking algorithms are able to process specific frame sequences with different sharpness values better or more quickly than others. The eye tracking device also may comprise a button, switch or other user interface for selecting an option for higher precision eye tracking and if the user notices the eye tracking device by means of this interface, the eye tracking device can switch to a mode, in which the imaging properties like the focal length are varied to achieve this higher eye tracking precision.

According to the method for operating an eye tracking device according to the invention, the eye tracking device comprises an optical system, wherein the capturing unit of the optical system captures images of at least one part of at least one eye of a user and a processing unit of the eye tracking device determines at least one property of at least one eye on the basis of the captured images, wherein the capturing unit captures a first image and a second image of the at least one part of the eye of the user, and wherein the eye tracking device comprises an optical system. This optical system comprises an imaging property comprising at least one first imaging property and a second imaging property different from the first imaging property, wherein the optical system provides a first optical path with a first imaging property and a second optical path with a second imaging property, wherein the capturing unit captures the first image by capturing light that has passed along the first optical path and the second image by capturing light that has passed along the second optical path, so that due to the difference of the first and second imaging property the first image and the second image comprise a difference related to a characteristic of the at least one part of the first and second image, wherein the processing unit determines the at least one property of the eye on the basis of at least one of the first image and the second image.

The preferred embodiments and advantages described with regard to the eye tracking device according to the invention correspondingly apply to the method according to the invention. Especially the eye tracking device according to the invention can be used for performing the method according to the invention. Furthermore, described embodiments of the eye tracking device according to the invention constitute further steps of the method according to the invention.

In the following, advantageous embodiments of the present invention are described in more detail with reference to the accompanying drawings.

They show in.

Figure 1:
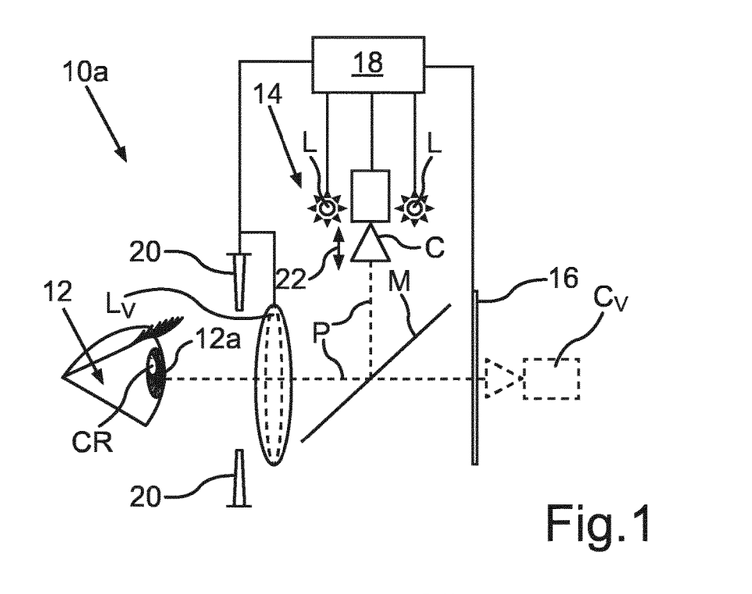
FIG. 1 a schematic illustration of an eye tracking device according to a first embodiment of the invention.

FIG. 1 shows a schematic illustration of an eye tracking device 10a according to an embodiment of the invention, which in this case is configured as a head-mounted eye tracking device. The eye tracking device 10a comprises a capturing unit C, which may comprise one or more cameras or image sensors for capturing images of the eye 12 of a user, e.g. wearing the head-mounted eye tracking device. Furthermore, the capturing unit C is part of an optical system 14 of the eye tracking device, wherein the optical system 14 may comprise one or more optical elements, like lenses, prisms, mirrors, beam splitters and so on. In this example, the optical system 14 comprises a varifocal lens $L_V$, which has a variable focal length. Moreover, the eye tracking device 10a can optionally comprise one or more light sources L, of which two are shown in FIG. 1 exemplarily. As further optional components the eye tracking device 10a can comprise a hot mirror M and a display device 16. Moreover, the eye tracking device 10a comprises a processing unit 18 for processing the captured images and determining at least one feature of the eye 12, for example a gaze direction. Additionally, the processing unit 18 may control the light sources L, the display device 16, the variable focus lens $L_V$ and the opening of an aperture diaphragm 20 of the eye tracking device 10a.

The variable focus lens $L_V$ is placed between the capturing unit C and the user's eye 12 with regard to the optical path P from the eye 12 to the capturing unit C, so that at least some eye features in the image captured by the capturing unit C may be altered in their appearance in the captured images, e.g. in their form, size and/or position. For example, the varifocal lens $L_V$ between the capturing unit C and the eye 12 can magnify the pupil 12a in the captured image.

The light sources L can produce reflections on the cornea, so-called cornea reflections CR, especially in a structured way, like in an annular form, in a point-like way and/or circle-like way. The light path from the light sources L to the eye 12 in this setup is also altered by the optical system 14, especially by the varifocal lens $L_V$. In particular, in this configuration the light emitted by the light sources L is also reflected by the mirror M, passes through the varifocal lens $L_V$ and impinges on the eye 12. The images captured by the capturing unit C are processed by the processing unit 18 and features of the eye 12 are detected, on the basis of which e.g. the gaze direction can be calculated.

The hot mirror M provides more flexibility with regard to the positioning of the capturing unit C and the light sources L and still makes a central view of the capturing unit C onto the eye 12 possible. This is illustrated by the virtual camera $C_V$. The view of the capturing unit C corresponds to the view of a camera at the position of the virtual camera $C_V$ without the mirror M. Moreover, in this case the light sources L emit light at least in part in the IR spectral range and the hot mirror M is configured to reflect Light in the IR spectral range and transmits light in the visible spectral range, so that the user has an unobstructed view on the display 16.

In other embodiments of invention, for example for a different use of the eye tracking device 10a, for example for medical or diagnostic purposes, the capturing unit 10 could also be placed in the position of the shown virtual camera $C_V$ and the mirror M and the display device 16 can be omitted. The capturing unit C can also comprise more than one camera or image sensors in different places. The capturing unit C could also be placed to have direct view onto the eye 12 without having any element of the optical system 14 in between and only the light sources L are placed such that the light path from the light sources L to the eye 12 passes through the varifocal lens $L_V$. On the other hand, also the light sources L could be placed such that they illuminate the eye 12 directly without having the optical system 14 in between and the capturing unit C is positioned as shown.

The optical system 14 of the eye tracking device 10a is configured to provide different imaging properties. These different imaging properties again can be provided by variation of one or more elements of the optical system 14. For example, the focal length of the variable focus lens $L_V$ can be varied, which results in different magnifications of the captured image. A variation of the focal length also results in a variation of the focal plane, which is the plane in which the object, in this case the eye 12, is imaged in focus. The image properties can also be influenced by the opening of the aperture diaphragm 20, wherein a large opening results in a small depth of field and a small opening results in a large depth of field. Optionally, the optical system 14 may also comprise elements which are variable in their position. For example, the capturing unit C, or at least one part thereof, like the image sensor, may be mounted variable in its position, which shall be illustrated in FIG. 1 by the arrow 22. This way, the image sensor can be moved and varied in its position with regard to the focal plane, which results in different sharpness of the captured images. These different settings of the different components of the optical system 14, like different values of the aperture 20, different focal lengths of the varifocal lens $L_V$ or the different positions of the image sensor of the capturing unit C, are in the following denoted as different settings of the optical system 14.

These different settings of the optical system 14 can now advantageously be used for enhancing the eye tracking quality. For example, by means of the variable focus lens $L_V$ and the variable position of the capturing unit C, enlarged and sharp images of the eye 12 can be provided when at the same time having a large opening of the aperture diaphragm 20. Due to this large aperture opening, more light can be captured, which enhances the image quality and therefore positively influences the eye tracking results. Also by means of capturing unsharp images, the eye tracking quality can be enhanced, as unsharp images can be used for more accurately determining the position of cornea reflections CR. This is due to the fact that usually cornea reflections CR appear in an image only as very small bright points. If, however, unsharp images of the eye 12 are captured, these cornea reflections CR appear blurry and therefore enlarged like bright circles. Therefore, their contours and especially their centres, which finally define the position of the cornea reflections CR, can be determined more accurately. The possibility of providing different imaging properties, however, can be used in a different scenario, as shown in FIG. 1 in a highly advantageous way.

As shown in FIG. 1, the primary function of the variable focus lens $L_V$ is not only to provide different imaging properties for eye tracking, but also to provide different imaging properties for displaying or projecting the display image on the display device 16 as virtual image at a certain distance to the user's eye 12. In this scenario, the display device 16 may be configured as stereo image display device for displaying three-dimensional images to both eyes 12 of the user. The variable focus lens $L_V$ can be used to display the image shown on the display device 16 as virtual image at a distance of the user's eye 12, which corresponds to the distance at which the user's eyes 12 are accommodated, which therefore results in very natural vision. So by means of the varifocal lens $L_V$ accommodation cues can be produced corresponding to the accommodation of the user's eyes. Therefore, the variable focus lens $L_V$ is primarily used to vary the position of the virtual image of the display device 16 in dependency on the 3D gaze point of the user, which can again be determined by means of the eye tracking device 10a. Additionally and at the same time, the variable focus lens $L_V$ can be used for optimizing the eye tracking quality, as explained above. Moreover, it has to be noted that if the lens $L_V$ is controlled in dependency of the determined gaze point or accommodation cue to project images at a certain distance to the users eye, this may lead to unsharp images captured by the capturing unit C. Such unsharp images can then be used to deterring the position of the cornea reflections. Moreover, also the position of the image sensor of the capturing unit C can be moved correspondingly to get sharp images and to control the image characteristics additionally to the controlling of the varifocal lens $L_V$. So the varifocal lens cannot only be used for producing correct accommodation cues, but at the same time variations of the focal length can be used to improve the 3D reconstruction of the eye.

Figure 2A:
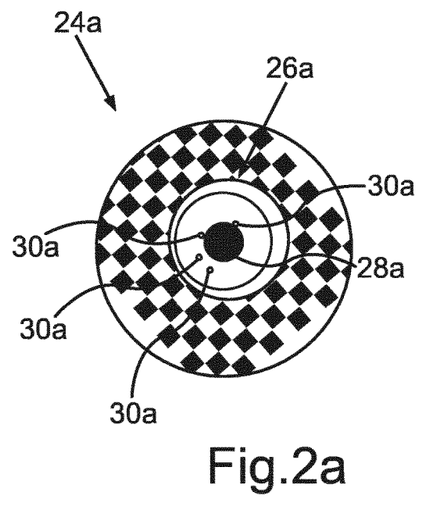
FIG. 2a a schematic illustration of a first image captured by the capturing unit of the eye tracking device according to a first setting of the optical system of the eye tracking device.
Figure 2B:
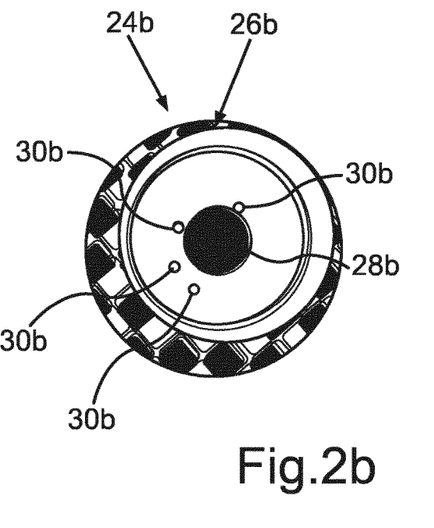
FIG. 2b a schematic illustration of a second image captured by the capturing unit of the eye tracking device according to a second setting of the optical system of the eye tracking device.

FIG. 2a shows a schematic illustration of a first image 24a captured by the capturing unit C with a first setting of the optical system 14 and FIG. 2b shows a schematic illustration of a second image 24b captured by the capturing unit C with a setting of the optical system 14. For illustrative purposes, these images 24a, 24b do not show a real eye but an artificial eye and a checkerboard, especially for different settings of the varifocal lens $L_V$, wherein the first image 24a was captured with a larger focal length than the second image 24b. This now results in a variety of different image characteristics, especially with regard to the image features relating to the eye 12, like the eye image 26a, 26b, the pupil image 28a, 28b and the cornea reflections image 30a, 30b. First of all, the imaged objects differ with regard to their size as for the second setting a larger magnification is provided than for the first one. Secondly, they differ with regard to their sharpness, as the focal plane has moved with regard to the image sensor plane. This again affects the contrast between image features and within image features. These images 24a, 24b also differ with regard to their brightness as due to the magnification, a smaller amount of light is distributed to the same pixel area of the image sensor in the second image 24b.

These differences in the image characteristics can now be used for a variety of different purposes. For example, the settings of the optical system 14 can be controlled such that the image characteristics are optimized for the purpose of eye tracking. Images with different characteristics can be subtracted to derive information about the position of contour points of imaged objects, a focus sweep and/or the change of size of features can be used to determine the object distance and also be used to determine the 3D position of imaged objects. The difference in image characteristics can also be used to derive information about the optical system 14 itself, like the current setting with regard to the focal length. Settings can be chosen for intentionally producing unsharp images, for example to blur out unwanted features or to more accurately determine the position or cornea reflections CR. The settings of the optical system 14 can also be chosen in dependency on the used eye tracking algorithm. So, overall, by providing an optical system 14, which makes it possible to constitute different imaging properties, a variety of advantages can be achieved, especially with regard to eye tracking.

Figure 3:
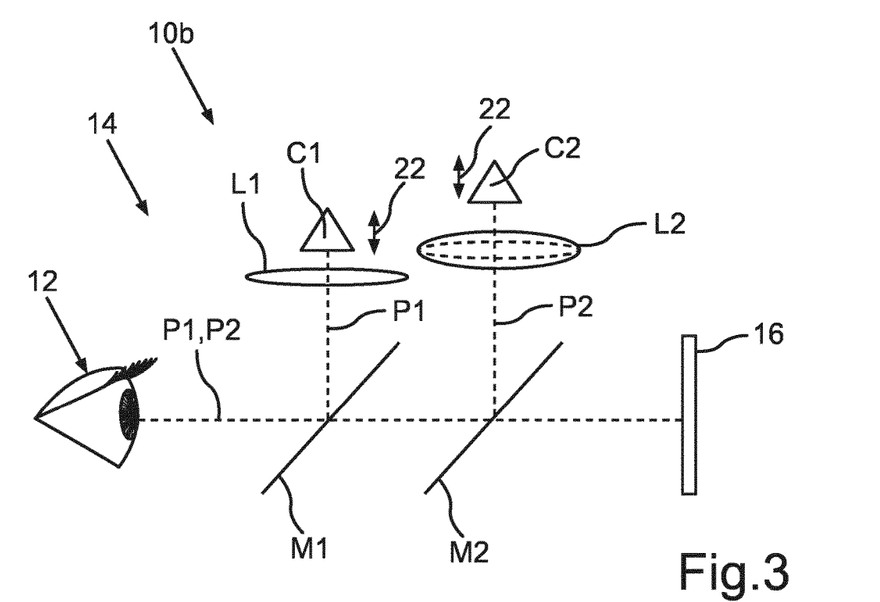
FIG. 3 a schematic illustration of an eye tracking device according to a second embodiment of the invention.
Figure 4:
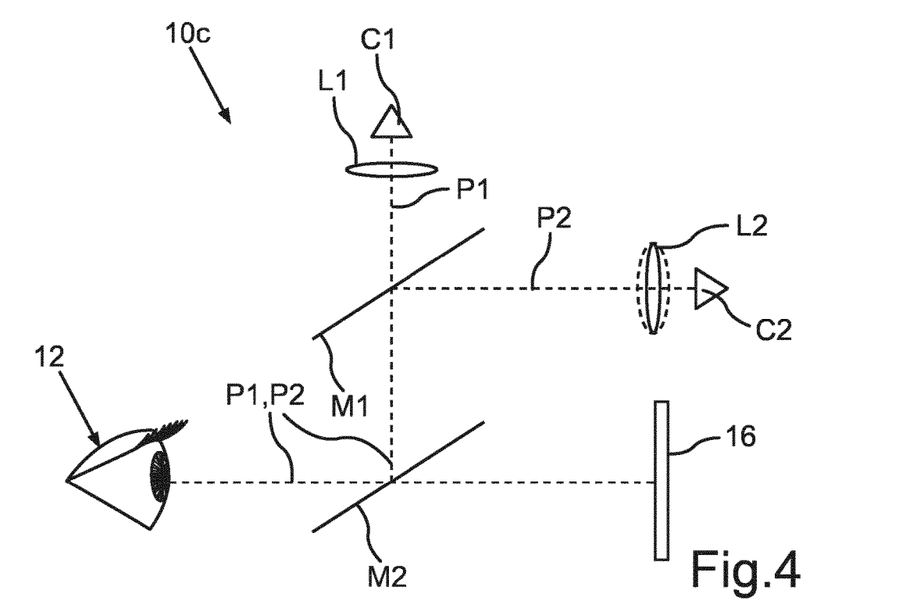
FIG. 4 a schematic illustration of an eye tracking device according a third embodiment of the invention.

Whereas FIG. 1 shows an embodiment of the invention in which different imaging properties are constituted timely successively, FIG. 3 and FIG. 4 show two further embodiments of the invention, in which different imaging properties are constituted at the same time by at least in part spatially separated optical paths P1, P2.

FIG. 3 shows a schematic illustration of a second embodiment of the eye tracking device 10b in a simplified manner. The eye tracking device also comprises the processing unit 18, and optionally light sources L or the aperture diaphragm 20 though their illustration in FIG. 3, and also in FIG. 4, has been omitted. In this case, the optical system 14 comprises two beam splitters M1, M2 to split up the optical path P1, P2 in two separate optical paths P1, P2. The capturing unit C in this case comprises two cameras C1, C2, wherein the first optical path P1 extends from the eye 12 to the first camera C1 and the second optical path P2 extends from the eye 12 to the second camera C2. The beam splitters M1, M2 can be configured such that they are transmissive for visible light and at least in part reflective for infrared light. Especially the first and second beam splitter M1, M2 may be transmissive for visible light. Moreover, the first beam splitter M1 may partially reflect infrared light and partially transmit infrared light, wherein the transmitted infrared light is then reflected by the second beam splitter M2, especially totally. In each optical path P1, P2, a lens L1, L2 is positioned for providing different imaging properties in the respective optical paths P1, P2. For this purpose, the first lens L1 may comprise a different focal length than the second lens L2. Also, it may be possible that the first lens L1 has a fixed predefined focal length, whereas the second lens L2 is configured as a variable focus lens with a variable focus length. Also in this case, the position of the respective cameras C1, C2 may be variable or at least the position of the respective image sensors, which shell again be illustrated by the arrows 22. So also by means of this setup, different image characteristics of the images captured by the respective cameras C1, C2 can be produced by providing different imaging properties in at least partially spatially separated optical paths P1, P2.

FIG. 4 shows another embodiment of the invention, in which the eye tracking device 10c comprises an optical system 14, also with two beam splitters M1, M2, however in a different position. Again in this setup, the capturing unit C comprises two cameras C1, C2 and a first optical path P1 extends from the eye 12 to the first camera C1 and a second optical path P2 extends from the eye 12 to the second camera C2. In each optical path P1, P2, a lens L1, L2 is positioned, wherein these lenses L1, L2 may have different focal lengths and/or be configured as variable focus lenses. Here again, the second beam splitter M2 is transmissive for visible light and fully reflective for infrared light, whereas the first beam splitter M1 is configured such that infrared light is in part transmitted and in part reflected to provide two separate paths P1, P2.

Moreover, these illustrated embodiments of the invention can also be combined in any arbitrary way. Even more than two separate paths can be provided, for example three, four, and so on, and any combination of beam splitters and variable focus lenses can be used. Also, it is possible to configure the eye tracking device as remote eye tracking device, for example by simply positioning a variable focus lens in front of the eye tracking camera. So, depending on the situation and the implementation of the eye tracking device, these embodiments of the invention provide a great degree of flexibility with regard to positioning the individual elements of the eye tracking device. Moreover, these embodiments provide great flexibility in splitting and positioning cameras, so that a variety of eye tracker designs can be realised.

Figure 5:
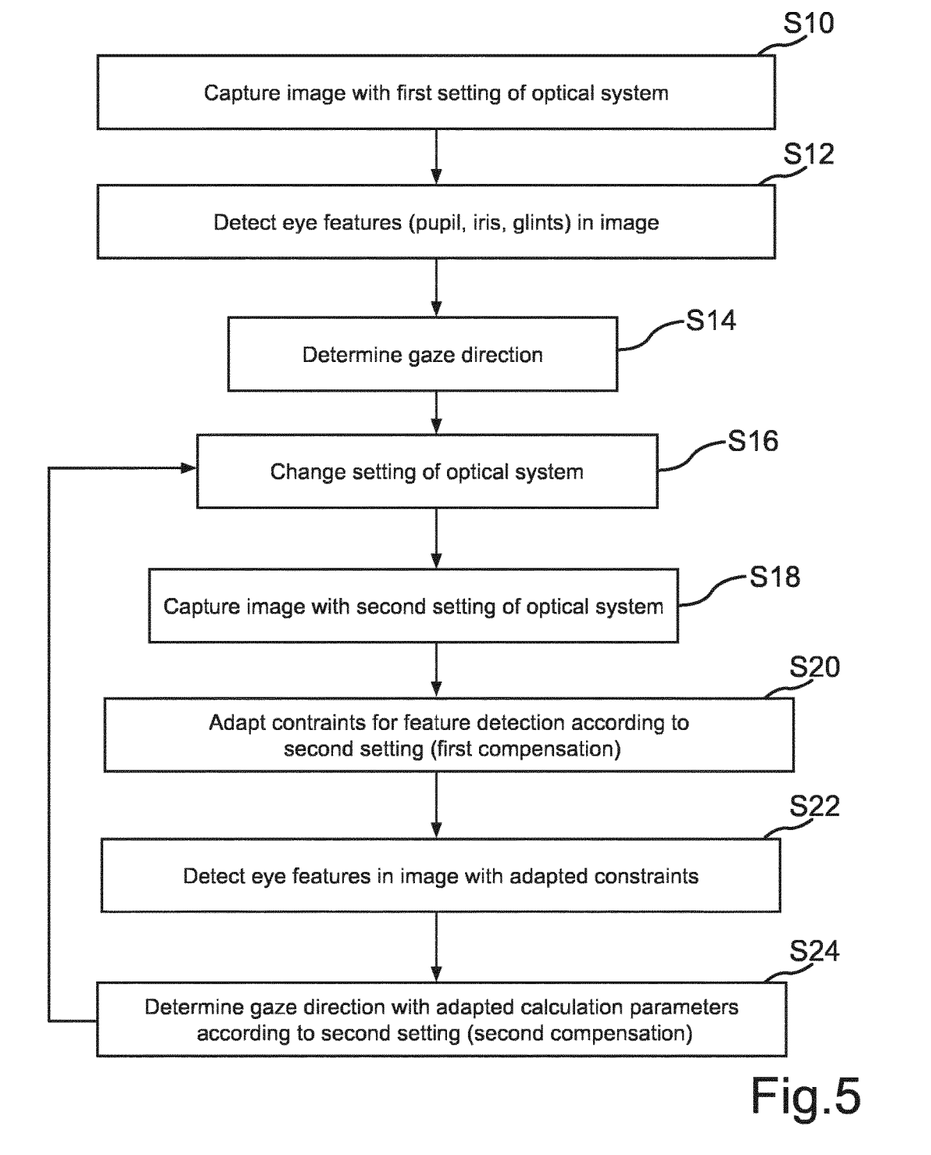
FIG. 5 a flow chart illustrating a method for operating an eye tracking device according to an embodiment of the invention.

FIG. 5 shows a flow chart for illustrating a method for operating the eye tracking device according to an embodiment of the invention. This method may be performed by an eye tracking device 10a shown in FIG. 1. So, first, an image is captured with a first setting of the optical system 14 in S10. This first setting may correspond to a standard setting of the optical system or a reference setting or the like. In S12, eye features, like the pupil 12a, the pupil contour points, the pupil centre, the iris, the iris centre, glints or cornea reflections CR, and so on are detected in the captured image. On the basis of these detected eye features in the image, the gaze direction can be determined in S14.

Now, the setting of the optical system 14 may be changed in S16 and another image with the new and different setting of the optical system 14 is captured in S18. However, as different settings of the optical system 14 have influence on the appearance of the objects in the image, this change in appearance has to be considered when doing eye tracking, as otherwise this would result in a wrong or incorrect determination of the position of eye features and the finally calculated gaze direction. Therefore, in S20 the eye tracking device adapts the constraints for feature detection according to the second setting. Usually, the processing unit 18 searches in the captured images for example for elliptical dark regions of a certain size to identify a pupil in the captured image. As, however, the size of eye features may change due to the change of the setting of the optical system 14, this size constraint needs to be adapted to the current setting. Depending on the change of the setting of the optical system 14, also other constraints, for example with regard to the shape of eye features, namely their geometrical form, with regard to brightness, saturation, spectrum, etc. can be adapted as well. By means of this constraint adaption, a first compensation is provided, compensating the effects of the change in the imaging properties on the appearance of captured eye features in the image. The processing unit 18 can now detect eye features in S22 in the image according to the adapted constraints. After that, in S24 the gaze direction can be determined. Also here, the change in the setting of the optical system has to be taken into account, which advantageously can be done by adapting the calculation parameters according to the second setting. Thereby it can be avoided for example that an enlarged image of the eye is mistakenly interpreted as the eye being moved closer to the optical system 14. Therefore, the current settings of the optical system 14, like the zoom factor, focal length and the like, can be taken into account when calculating the positions of the detected eye features and therefrom calculating the gaze direction. So by adapting the calculation parameters in dependency of the current setting, a second compensation can be provided. After that, this procedure can be repeated, for example by going back to S16 and choosing a new setting again.

Figure 6:
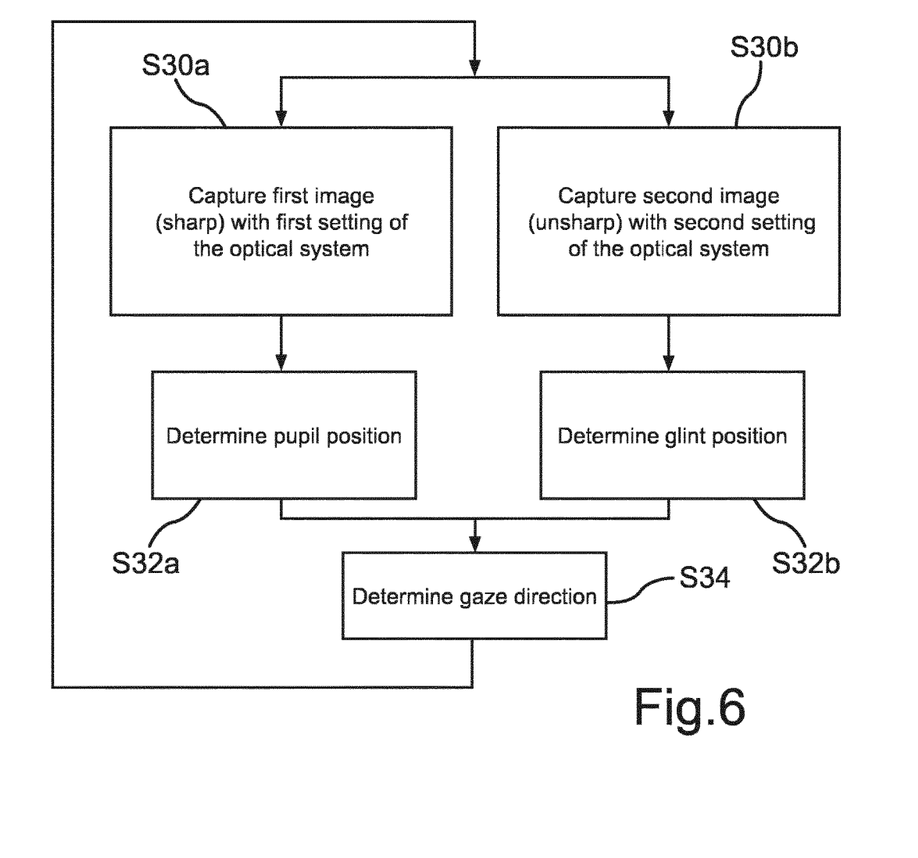
FIG. 6 a flow chart illustrating a method for operating an eye tracking device according to another embodiment of the invention.

FIG. 6 shows another flow chart for illustrating a method for operating an eye tracking device 10a, 10b, 10c according to another embodiment of the invention, which can also be combined with the method shown in FIG. 5. According to this procedure, the eye tracking device 10a, 10b, 10c captures a first image with a first setting of the optical system 14 in S30a, especially such that this image has high sharpness. Moreover, the capturing unit of the eye tracking device captures a second image with a second setting of the optical system 14 in S30b, especially such that the image comprises a lower sharpness than a first image. The first and second image can be captured timely successively, for example by means of the eye tracking device 10a shown in FIG. 1 or also at the same time by means of an eye tracking device 10b, 10c shown in FIG. 4 or FIG. 3. The first image can then be used to determine the pupil position, wherein the unsharp image is used to determine the glint position, namely the position of the cornea reflections CR produced by light sources L of the eye tracking device 10a, 10b, 10c. On the basis of the determined pupil position in S32a and the determined glint position in S32b, the gaze direction can be determined in S34 and the procedure can start again in S30a and S30b. Due to e.g. an alternation with regard to capturing of sharp and unsharp images with respect to the eye, much more reliable and accurate eye tracking results can be achieved. Especially, a defocus to create a bokeh, which denotes the unsharp mostly circular appearance of out-of-focus objects in an image, of virtual light sources such as reflections on the cornea CR allows for a more precise localization. Also, a quick alternation between focal depths can be used especially to create highly focussed images of the pupil and defocused images of the cornea reflections CR to achieve high precision and accuracy of the determined gaze direction. Also the difference of the cornea reflections CR in the two images can be used, e.g. by subtracting first and second image from each other, to optimize the contour detection (difference of images captured at different focal lengths, difference of Gaussians).

In total an eye tracking device or system and method for eye tracking can be provided that allows for dynamic varifocal and/or multifocal image capturing, especially means of an optical system whose effective focal length can be adapted/altered, and therefore can improve gaze precision and accuracy, the building of a physiological model of the eye, e.g. using focus sweep to estimate the depth of features, and allows to make better use of the available light by allowing for larger apertures (=faster lenses). By means of the invention e.g. the sharpness of the eye and possibly reflections/features for different tracking scenarios can be optimized, e.g. by an algorithm specific optimization, or an optimization for higher gaze accuracy and/or precision and physiognomy.

The eye tracking device and/or method can highly improve the detection/determination of eye features in captured image(s) such as:
reflection(s) (e.g. Purkinje image) on the at least one eye's surface or parts hereof, e.g. a corneal reflection (CR) is a reflection on the cornea of the at least one eye
pupil of at least one eye as an area in the captured image which is detectable as area belonging to the pupil of the eye
limbus
cornea
eye ball
sclera
iris
blood vessels
one of the Purkinje reflections of $1^{st}$ to $4^{th}$ order.

Each of the above mention eye features can be described further, e.g. by 2D position and/or 3D pose, shape, texture, contrast, sharpness, colors, edges, spectrum, polarization, correlations, gradients, and/or distributions of the aforementioned properties of the above mentioned eye features.

The eye tracking device further allows to optimize measure criteria, like gaze precision, gaze accuracy, feature precision, feature accuracy, feature (un-)certainty (measure to quantify how (un)certain the algorithm can be about value(s) for a property of an eye feature, e.g. derived from spatial differences in form of position and shape for a feature identified in images), sharpness of image/edges (image processing criteria to assess 'quality' of current situation for eye tracking), contrast, intra and inter feature contrast ratio, by optimizing the setting of the optical system/or choose the part of the image (e.g. in case of beam splitter), which optimizes criteria for at least one feature. E.g. if edges are too fuzzy for pupil detection, the focal length is adapted until detected pupil/pupil confidence is considered good. The invention can also be used for many other different purposes like using shallow depth of field to blur out unwanted features, using the history of one of more previously reported optical system status or properties or the properties of simultaneously acquired images to derive information, like depth, orientation, sharpness, confidence, focal length and so on.

LIST OF REFERENCE SIGNS 10a, 10b, 10c eye tracking device
12 eye
12a pupil
14 optical system
16 display device
18 processing unit
20 aperture diaphragm
22 arrow
24a first image
24b second image
26a, 26b eye image
28a, 28b pupil image
30a, 30b cornea reflection image
CR cornea reflection
C capturing unit
$C_V$ virtual camera
C1 first camera
C2 second camera
M hot mirror
M1 first beamsplitter
M2 second beamsplitter
P optical path
P1 first optical path
P2 second optical path
L light source
$L_V$ variable focus lens
L1 first lens
L2 second lens

The invention claimed is:
1. A method comprising:
capturing a first image of an eye of a user with a first focal length providing a first sharpness of the first image;

capturing a second image of the eye of the user with a second focal length different from the first focal length providing a second sharpness of the second image less than the first sharpness of the first image;

determining a position of a pupil of the eye of the user based on the first image having the first sharpness;

determining a position of a corneal reflection on a cornea of the eye of the user based on the second image having the second sharpness less than the first sharpness; and determining a gaze direction of the user based on the position of the pupil and the position of the corneal reflection.

2. The method of claim 1, wherein the first image and the second image are captured simultaneously.

3. The method of claim 1, wherein the first image and the second image are captured in temporal succession.

4. The method of claim 1, wherein capturing the first image comprises setting a focal length of a varifocal lens to obtain the first image having the first sharpness and wherein capturing the second image comprises setting the focal length of the varifocal lens to obtain the second image having the second sharpness less than the first sharpness.

5. The method of claim 1, wherein capturing the first image comprises capturing the first image of eye of the user along a first path and wherein capturing the second image comprises capturing the second image of the eye of the user along a second path that is partially overlapping the first path and partially spatially separated from the first path.

6. The method of claim 1, wherein capturing the second image comprises:
   determining one or more eye features of the user based on the first image; and
   determining the second focal length based on the one or more eye features.

7. An eye tracking device comprising:
   an imaging system to capture a first image of an eye of a user with a first focal length providing a first sharpness of the first image and to capture a second image of the eye of the user with a second focal length different from the first focal length providing a second sharpness of the second image less than the first sharpness of the first image; and
   a processor to determine a position of a pupil of the eye of the user based on the first image having the first sharpness, determine a position of a corneal reflection on a cornea of the eye of the user based on the second image having the second sharpness less than the first sharpness, and determine a gaze direction of the user based on the position of the pupil and the position of the corneal reflection.

8. The eye tracking device of claim 7, wherein the imaging system is to capture the first image and the second image simultaneously.

9. The eye tracking device of claim 7, wherein the imaging system is to capture the first image and the second image in temporal succession.

10. The eye tracking device of claim 7, wherein the imaging system comprises a varifocal lens and the processor is to set a focal length of a varifocal lens to obtain the first image having the first sharpness and to set the focal length of the varifocal lens to obtain the second image having the second sharpness less than the first sharpness.

11. The eye tracking device of claim 7, wherein the imaging system is to capture the first image along a first path and to capture the second image along a second path that is partially overlapping the first path and partially spatially separated from the first path.

12. The eye tracking device of claim 11, wherein the imaging system includes a beam splitter that spatially separates the first path and the second path.

13. The eye tracking device of claim 7, wherein the processor is to:
   determine one or more eye features of the user based on the first image;
   determine the second focal length based on the one or more eye features; and
   set a varifocal lens of the imaging system to capture the second image with the second focal length.

14. A non-transitory computer-readable medium encoding instructions which, when executed, cause a processor to perform operations comprising:
   capturing a first image of an eye of a user with a first focal length providing a first sharpness of the first image;
   capturing a second image of the eye of the user with a second focal length different from the first focal length providing a second sharpness of the second image less than the first sharpness of the first;
   determining a position of a pupil of the eye of the user based on the first image having the first sharpness;
   determining a position of a corneal reflection on a cornea of the eye of the user based on the second image having the second sharpness less than the first sharpness; and
   determining a gaze direction of the user based on the position of the pupil and the position of the corneal reflection.

15. The non-transitory computer-readable medium of claim 14, wherein capturing the first image comprises setting a focal length of a varifocal lens to obtain the first image having the first sharpness and wherein capturing the second image comprises setting the focal length of the varifocal lens to obtain the second image having the second sharpness less than the first sharpness.

16. The method of claim 1, wherein the first image is a sharp image and the second image is an unsharp image.

17. The method of claim 1, wherein the first image is in-focus and the second image is out-of-focus, creating a bokeh in the second image.

18. The method of claim 1, wherein determining the position of the corneal reflection on a cornea of the eye of the user based on the second image includes:
   determining a plurality of contour points of the corneal reflection;
   fitting an ellipse to the plurality of contour points; and
   determining a center of the ellipse.

19. The method of claim 1, wherein determining a position of a corneal reflection on a cornea of the eye of the user based on the second image includes subtracting the first image and the second image from each other.

* * * * *